United States Patent
Chatellier et al.

(10) Patent No.: US 7,950,283 B2
(45) Date of Patent: May 31, 2011

(54) ULTRASOUND PREDICTION OF WORKPIECE DEFORMATION

(75) Inventors: Jean-yves Francois Roger Chatellier, Arcueil (FR); Eric Charles Louis Le Letty, Saint Genevieve des Bois (FR)

(73) Assignee: SNECMA, Paris (FR)

( * ) Notice: Subject to any disclaimer, the term of this patent is extended or adjusted under 35 U.S.C. 154(b) by 385 days.

(21) Appl. No.: 12/128,302

(22) Filed: May 28, 2008

(65) Prior Publication Data
US 2008/0295601 A1 Dec. 4, 2008

(30) Foreign Application Priority Data
May 29, 2007 (FR) ..................... 07 03772

(51) Int. Cl.
*G01N 29/07* (2006.01)
(52) U.S. Cl. ............... 73/602; 73/597; 73/598; 73/600
(58) Field of Classification Search .......... 73/602, 73/596, 624, 629, 597, 598, 599, 600, 620, 73/627, 628; 702/35
See application file for complete search history.

(56) References Cited

U.S. PATENT DOCUMENTS

| | | | | |
|---|---|---|---|---|
| 4,573,358 A * | 3/1986 | Luongo | ........... | 73/660 |
| 5,386,727 A | 2/1995 | Searle | | |
| 6,105,431 A * | 8/2000 | Duffill et al. | ........... | 73/624 |
| 6,594,619 B1 * | 7/2003 | von Flotow | ........... | 702/184 |
| 6,785,635 B2 * | 8/2004 | von Flotow | ........... | 702/184 |
| 6,889,551 B2 * | 5/2005 | Andrews et al. | ........... | 73/597 |
| 6,996,497 B2 * | 2/2006 | Floyd et al. | ........... | 702/181 |
| 7,104,120 B2 * | 9/2006 | Gladden | ........... | 73/114.77 |
| 7,493,809 B1 * | 2/2009 | Ward, Jr. | ........... | 73/168 |
| 7,509,862 B2 * | 3/2009 | Cohen et al. | ........... | 73/660 |
| 2008/0206057 A1 * | 8/2008 | Twerdochlib | ........... | 416/190 |

FOREIGN PATENT DOCUMENTS

| | | |
|---|---|---|
| DE | 197 12 650 A1 | 10/1998 |
| FR | 1 416 636 | 11/1965 |
| GB | 2 383 413 A | 6/2003 |
| WO | WO 96/36874 | 11/1996 |

* cited by examiner

*Primary Examiner* — Jacques M Saint Surin
(74) *Attorney, Agent, or Firm* — Oblon, Spivak, McClelland, Maier & Neustadt, L.L.P.

(57) ABSTRACT

A method of predicting workpiece deformation prior to machining that causes the workpiece to deform through release of residual stresses. The method includes emitting a beam of ultrasound waves onto the workpiece surface in such a way that a longitudinal wave is propagated in a given direction under and substantially parallel to the surface, positioning at least one transducer in receive mode on the surface to receive a subsurface longitudinal wave that has been propagated, and measuring the propagation velocity of the subsurface longitudinal wave. The method further includes performing these steps in two workpiece regions, a first region sensitive to residual stresses and a second region somewhat insensitive to residual stresses, then calculating a difference in propagation velocity between the velocity measured in the first region and the velocity measured in the second region and from the difference, deducing the deformation that will result from machining the first region.

13 Claims, 1 Drawing Sheet

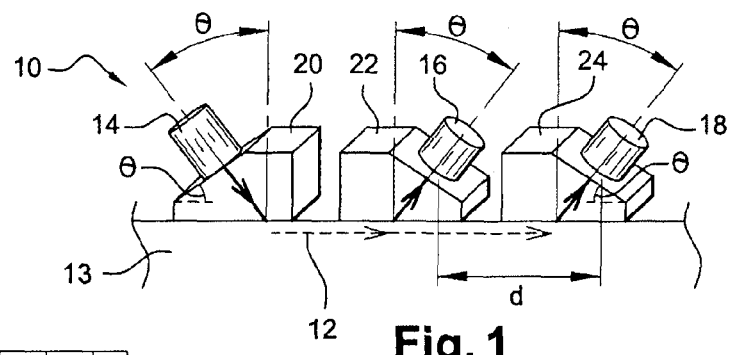
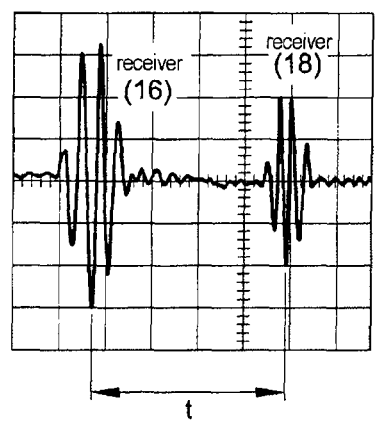
Fig. 2
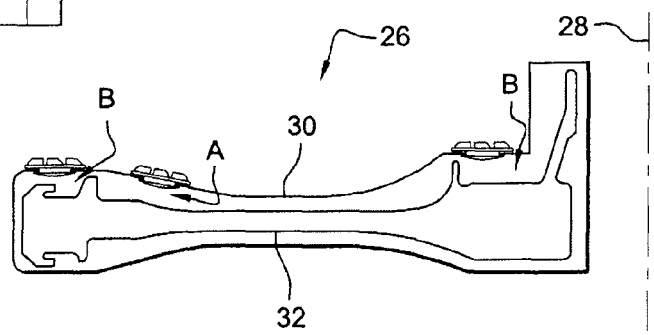
Fig. 3
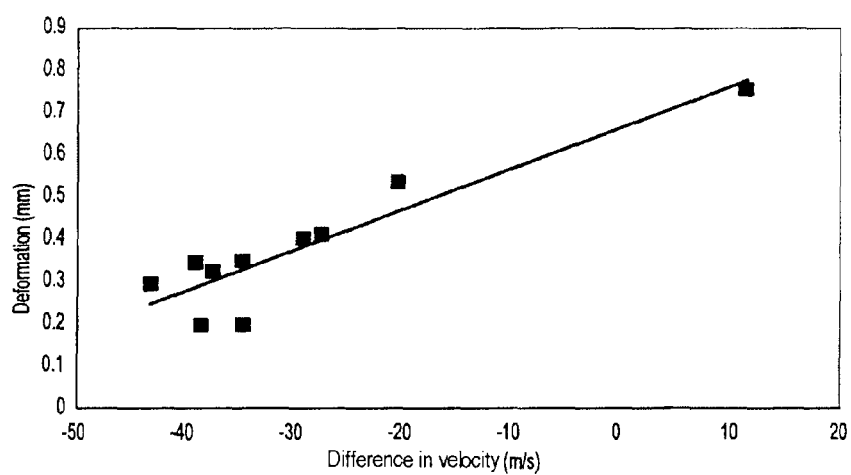
Fig. 4

ULTRASOUND PREDICTION OF WORKPIECE DEFORMATION

BACKGROUND OF THE INVENTION

The present invention relates to a method of predicting the deformation of a workpiece that is to be subjected to a machining operation and, in particular, relates to an application of this method to a high-pressure compressor disk in a turbomachine.

The production of parts such as compressor disks usually entails several machining operations. Now, during machining, the workpiece may become deformed as a result of residual stresses present in the workpiece being released. When the deformation exceeds a certain value, the tolerances in terms of thickness, flatness and parallelism for example are no longer met and thus cause the machined workpiece to be scrapped, leading to significant financial losses.

DESCRIPTION OF THE PRIOR ART

In order to reduce the impact of the residual stresses during the machining operations, it is possible to carry out a larger number of machining operations in order to be able to limit the deformation. However, increasing the number of machining operations entails a significant additional cost because of the relatively lengthy time needed for each machining operation. Experience gained with machining does not allow the most suitable procedure to be deduced because the level of deformation varies greatly between workpieces of the same type.

SUMMARY OF THE INVENTION

It is a particular object of the invention to provide a method for estimating the deformation of a workpiece before it is machined, this method being simple to implement, effective and economical.

To this end, the invention proposes a method of predicting the deformation of a workpiece that will be subjected to machining, liable to cause deformation of the workpiece through the release of residual stresses in the workpiece, which method consists in:

a. emitting a beam of ultrasound waves onto a surface of the workpiece, the beam being directed in such a way that a longitudinal wave is propagated in a given direction under the surface of the workpiece and substantially parallel to the surface, b. positioning at least one transducer in receive mode on the surface of the workpiece to receive the subsurface longitudinal wave that has been propagated, c. measuring the propagation velocity of the subsurface longitudinal wave, d. steps a to c being performed in two different regions of the workpiece, the first region being sensitive to residual stresses and the second region being somewhat insensitive to residual stresses, then calculating the difference between the velocity measured in the first region and the velocity measured in the second region and from this difference deducing the deformation that will result from machining the first region of the workpiece.

The use of a longitudinal wave propagating under the surface of the workpiece allows the part of the workpiece that is to undergo machining to be assessed. The velocity of the subsurface longitudinal wave, which is sensitive to the residual stresses, provides information regarding the stress levels in the region sensitive to residual stresses by comparison with a reference velocity measured in a region of the workpiece that is not sensitive to residual stresses. The invention allows the deformation of the workpiece to be deduced from the difference in propagation velocity. It is thus possible to anticipate how the workpiece will deform as a result of it being machined.

According to another feature of the invention, this method consists beforehand in producing a calibration curve of deformation as a function of the difference in velocity of propagation of the subsurface longitudinal wave by carrying out steps a to d on a plurality of similar workpieces then performing the machining operation and measuring the deformation of the workpieces and in using this calibration curve to predict the deformation of an unmachined workpiece from the difference in velocity in step d calculated for this workpiece.

According to the propagation equations, the difference in velocity varies with stress. The method according to the invention proposes to link this difference in velocity directly to the deformation obtained after machining without performing lengthy and complicated calculations regarding the stress field. The calibration curve of deformation as a function of the difference in velocity between the regions that are sensitive and insensitive to stress thus, by a simple and quick measurement of the difference in velocity, makes it possible to predict how the workpiece will deform, this representing a considerable advantage over the prior art.

In a preferred embodiment of the invention, the method uses two transducers in receive mode having parallel ultrasound axes and which are separated by a known distance.

By using two transducers in receive mode, velocity of the subsurface longitudinal wave can thus be measured by measuring the difference in transit time between the echoes received at each of the two transducers. A measurement such as this is simpler to implement than a measurement of the transit time between an emitting transducer and a receiving transducer which entails perfect knowledge of the instant at which the emitting transducer emits a wave.

Advantageously, the method also consists in interposing a coupling piece between each transducer and the unmachined workpiece.

Interposing a coupling piece between the surface of the workpiece and the transducers ensures correct angular positioning of the transducer with respect to the workpiece. It also makes it possible to get around the need to immerse the workpiece and the transducers in a vat of liquid in order to generate a subsurface longitudinal wave. In addition, immersing parts such as turbomachine disks is not always feasible given the sometimes large dimensions thereof.

According to another feature of the method, the coupling piece comprises at least one inclined plane forming an angle θ with respect to the surface of the workpiece when the coupling piece is interposed between the transducer and the workpiece.

The emission and reception coupling pieces are positioned on the surface of the workpiece in such a way that their inclined planes are directed in the counterclockwise and clockwise directions with respect to the surface of the workpiece, respectively, the transducers being positioned in such a way that their ultrasound axes are perpendicular to the inclined planes of their coupling pieces.

Positioning the transducers on their coupling pieces in this way allows their ultrasound axes to form an angle θ with the surface of the workpiece. The angle of incidence θ of the ultrasound beam on the workpiece determines whether or not a subsurface longitudinal wave will be propagated. This angle, which is a function of the propagation velocities of the longitudinal waves through the coupling piece and through the workpiece being assessed can be determined experimentally.

The coupling piece may be made of a plastic such as polymethylmethacrylate (PMMA) and have a substantially triangular shape. In the case of PMMA, the angle θ that will allow the generation of a subsurface wave ranges between approximately 30° and 32°.

The method can be used with emitting and receiving transducers that have a central frequency ranging between 1 and 15 MHz. The choice of frequency determines the thickness, in the workpiece, of the region of propagation of the subsurface longitudinal wave. If the level of stress in the workpiece is to be analyzed over a considerable depth, then a low frequency will be chosen, and vice versa if a shallower thickness is to be analyzed.

In order to measure the deformation of the workpiece, sensors may be positioned on the workpiece.

The method according to the invention may be applied to a turbomachine compressor disk and the ultrasound velocity measurements are performed with emitting and receiving transducers radially aligned on the surface of the disk that is to be machined. Positioning the transducers on a radial line can be justified through the fact that the difference in velocity calculated in this direction correlates well with the deformation of the workpiece.

The method finally consists in determining a number of machining operations from the deformation value deduced from the difference in velocity calculated in step d.

Depending on the deformation value predicted by the method, a decision may be taken to carry out a small number of machining operations if the predicted value is low or, in the case of a higher predicted deformation value, a decision may be taken to increase the number of machining operations in order to release the residual stresses more gradually. A decision may also be taken to subject the workpiece to an additional stress relieving treatment if so doing will make it possible to avoid scrapping the workpiece. Finally, the decision may be made not to machine the workpiece if the predicted amount of deformation is too great.

This methodology makes it possible to make the best choice as to the number of steps needed to machine a workpiece and leads to considerable savings in terms of time and in terms of economics.

BRIEF DESCRIPTION OF THE DRAWINGS

The invention will be better understood and further details, advantages and features of the invention will become apparent from reading the following description which is given by way of nonlimiting example with reference to the attached drawings in which:

FIG. 1 is a schematic perspective view of a device for measuring the velocity of a longitudinal wave propagated under the surface of a workpiece;

FIG. 2 shows two echoes received by the two receivers in the preferred embodiment of the invention;

FIG. 3 is a schematic view on a radial plane of half a turbomachine disk prior to machining;

FIG. 4 is a calibration graph showing deformation as a function of the difference in the velocities measured in regions of a turbomachine disk that are respectively sensitive and somewhat insensitive to residual stresses.

DESCRIPTION OF THE PREFERRED EMBODIMENT

Reference is made first of all to FIG. 1 which depicts a device 10 for measuring the velocity of an ultrasound subsurface longitudinal wave 12 (represented as dotted arrows) propagating through a workpiece 13. The device comprises an emitting transducer 14 and two receiving transducers 16, 18 positioned on coupling pieces 20, 22, 24 in such a way that their ultrasound axes are perpendicular to an inclined plane of their coupling pieces. The receiving transducers are separated by a known distance d. The inclined plane of the coupling piece 20 of the emitting transducer 14 makes an angle θ with the surface of the workpiece and this plane is directed in the counterclockwise direction. The inclined planes of the coupling pieces 22, 24 of the receiving transducers 16, 18 make the same angle θ with the surface of the workpiece and are directed in the clockwise direction. Thus, the ultrasound axis of each of the transducers also makes an angle θ with the surface of the workpiece. A coupling gel is inserted between the piezoelectric face of each of the transducers and the inclined plane and between the surfaces of the coupling piece and of the workpiece 13, thus ensuring the best possible coupling between the transducer, the coupling piece and the workpiece 13 and avoiding the artifacts that may be caused by the presence of air bubbles in the path along which the wave is propagated.

The transducers are connected to non-depicted control means such as a microcomputer.

When the emitting transducer 14 is excited by a generator (not depicted), the ultrasound wave emitted is propagated along the ultrasound axis of the transducer through the coupling piece 20 as far as the interface between the coupling piece 20 and the surface of the workpiece 13 and is refracted within the workpiece 13. A longitudinal wave is then refracted under the surface and propagates substantially parallel thereto. The subsurface longitudinal wave is radiated at an angle θ identical to the angle of incidence toward each of the receiving transducers 16, 18 through the coupling pieces 22, 24 and the received echoes are recorded (FIG. 2).

The velocity at which the ultrasound wave is propagated is measured by dividing the distance d separating the two receiving transducers 16, 18 by the measured time difference t between the echo received by the second receiver 18 and the echo received by the first receiver 16.

When a workpiece 13 is machined, the residual stresses in the workpiece may be released and therefore give rise to significant deformation of the workpiece which may then no longer meet the criteria or respect the tolerances required for use thereof, and has therefore to be scrapped.

It is therefore important, prior to machining, to know what level of stress is present in the material so that the machining operation can be optimally adapted to a gradual release of the residual stresses and to limiting deformation. The level of such stresses in a workpiece is directly proportional to the difference in propagation velocities of the ultrasound subsurface wave in a region sensitive to stress and in a region somewhat insensitive to stress. Thus, instead of carrying out a lengthy and complicated calculation on the stress field in order to establish a correspondence with the difference in velocity, the invention proposes to use the difference in propagation velocity of the subsurface longitudinal waves in order directly to estimate the deformation that the workpiece 13 will undergo during machining.

The workpiece 13 of which the deformation is to be evaluated in this instance is a high-pressure compressor disk 26 with an axis of symmetry 28 (FIG. 3). The continuous external outline 30 represents the surface of the disk 26 in the unmachined state and the continuous line 32 located inside the external outline 30 represents the final shape of the disk as obtained after machining.

The propagation velocity is measured using the abovementioned method in a region A lying between the radially internal and external end parts of the disk, which is known to be sensitive to stress. Similar measurements are taken in the two regions B that are somewhat insensitive to stress, these for example being located at the radially internal and external regions of the disk which are regions where there is a significant thickness of material. An incremental hole method, which consisted in making a hole in a workpiece by increments and in determining the residual stresses present deep within the material, confirmed that the stresses are very low in thick regions. In each of the regions A and B, the emitting and receiving transducers were aligned radially on the surface of the disk. Finally, the difference between the velocity measured in the region A and the mean of the velocities measured in the regions B was calculated.

The disk was then machined and its deformation after machining and unclamping measured using sensors, not depicted, positioned over the entirety of the disk.

This then gave a value for the difference in propagation velocity of the subsurface longitudinal wave that corresponded to an actual deformation due to the machining of the disk 26. Repeating the above operations a number of times on a plurality of disks 26 of the same type, yields several pairs of points [difference in velocity, deformation] that can be used to plot the calibration curve of FIG. 4 that represents the deformation as a function of the variation in the difference in velocity.

The linear regression of the deformation as a function of the difference in velocity shows an almost 84% correlation between the two variables, which is a highly satisfactory value.

In order to predict the deformation that a disk 26 of the same type will undergo as a result of machining, all that is required is for a velocity difference to be measured and for the corresponding deformation to be read off the calibration curve. In this way, it is possible to predict the deformation that the disk will experience during machining, with an accuracy of 0.1 mm.

It is then possible to adapt the number of machining operations to suit the predicted deformation value. For example, if the model predicts a deformation of less than 0.5 mm, then just two machining operations may be performed. If the predicted deformation ranges between 0.5 and 1 mm, then the number of machining operations can be increased, performing four such operations in order to release the stresses more gradually. If the predicted deformation is in excess of 1 mm, then a decision may be made to subject the disk 26 to an additional stress-relieving operation or alternatively, the decision may be taken to perform no further machining operations and to scrap the disk.

Employing such a strategy for machining thus makes it possible to limit the cost and the number of items scrapped.

The calibration curve obtained by the method is dependent on the machining parameters (the volume of material removed in each machining operation, the number of operations involving turning the workpiece over or round, etc.) because these parameters have a direct influence on the release of stress. Thus, the deformation scale obtained can be used only for certain machining parameters and for a given workpiece, which therefore means that the abovementioned experimental approach has to be repeated to obtain a calibration curve for some other type of workpiece and/or for different machining parameters.

In the embodiment depicted in the drawings, the receiving transducers 16, 18 are separated by a distance of 17.124 mm and the coupling pieces 20, 22, 24 are made of polymethylmethacrylate and are of trapezoidal shape. The angle of incidence θ that allows a subsurface longitudinal wave to be generated in the disk 26 therefore ranges between 30° and 32°. In practice, the velocities of the longitudinal wave in the disk were measured for an angle of 31.8°.

The coupling pieces may be made in any material other than polymethylmethacrylate provided that the magnitude of the angle θ is adapted to suit the propagation velocity of ultrasound in the coupling piece so that a subsurface longitudinal wave can be refracted in the workpiece 13.

The use of a coupling piece is not a prerequisite to the implementation of the method and the velocity measurements could be made by immersing the transducers and the workpiece in a liquid, the magnitude of the angle of incidence θ then ranging between 15° and 20° for a disk of the aforementioned type.

The ultrasound transducers adopted have a central frequency of 2.25 MHz so that the subsurface longitudinal wave is propagated under the surface over a thickness of about 6 mm. The frequency of the transducers may range between 1 and 15 MHz depending on how deeply the workpiece is to be assessed. For this frequency range, the thickness assessed is about 12 mm at 1 MHz and about 0.3 mm at 15 MHz.

The invention claimed is:

1. A method of predicting deformation of a workpiece that will be subjected to machining, liable to cause deformation of the workpiece through release of residual stresses in the workpiece, which method comprises:
    a. emitting a beam of ultrasound waves onto a surface of the workpiece, the beam being directed in such a way that a longitudinal wave is propagated in a given direction under the surface of the workpiece and substantially parallel to the surface,
    b. positioning at least one transducer in receive mode on the surface of the workpiece to receive a subsurface longitudinal wave that has been propagated,
    c. measuring a propagation velocity of the subsurface longitudinal wave, and
    d. performing steps a to c in two different regions of the workpiece, a first region being sensitive to residual stresses and a second region being somewhat insensitive to residual stresses, then calculating a difference in propagation velocity between a velocity measured in the first region and a velocity measured in the second region and from the difference, deducing a deformation that will result from machining the first region of the workpiece.

2. The method as claimed in claim 1 which further comprises:
    producing beforehand a calibration curve of deformation as a function of the difference in propagation velocity of the subsurface longitudinal wave by carrying out steps a to d on a plurality of similar workpieces,
    then performing a machining operation and measuring a deformation of the plurality of similar workpieces, and then
    using the calibration curve to predict a deformation of an unmachined workpiece from the difference in propagation velocity in step d calculated for the unmachined workpiece.

3. The method as claimed in claim 1 or 2, wherein the positioning includes two transducers in receive mode having parallel ultrasound axes and which are separated by a known distance.

4. The method as claimed in claim 1 further comprising:
    interposing a coupling piece between each transducer and the unmachined workpiece.

5. The method as claimed in claim 4, wherein the interposing includes a coupling piece having at least one inclined plane forming an angle θ with respect to the surface of the workpiece.

6. The method as claimed in claim 5, wherein the interposing includes an emission coupling piece and a reception coupling piece positioned on the surface of the workpiece, such that an inclined plane of the emission coupling piece and an inclined plane of the reception coupling piece are respectively directed in a counterclockwise and a clockwise direction to the surface of the workpiece, and wherein the positioning includes positioning an ultrasound axis of each transducer perpendicular to the inclined plane of the coupling piece of each transducer.

7. The method as claimed in claim 4, wherein the interposing includes a coupling piece made of polymethylmethacrylate and having a substantially triangular shape.

8. The method as claimed in claim 5, wherein the interposing includes a coupling piece having at least one inclined plane forming an angle θ that ranges between approximately 30° and 32°.

9. The method as claimed in claim 4 further comprising:
inserting a coupling gel between a piezoelectric face of each transducer and a surface of the coupling piece, and between another surface of the coupling piece and the surface of the workpiece.

10. The method as claimed in claim 1, wherein the positioning includes a transducer having a central frequency ranging between 1 and 15 MHz.

11. The method as claimed in claim 1 further comprising:
sensing deformation of the workpiece using several sensors positioned on the workpiece.

12. The method as claimed in claim 1, wherein the workpiece is a turbomachine compressor disk, and wherein the measuring the propagation velocity is performed with emitting and receiving transducers radially aligned on a surface of the disk that is to be machined.

13. The method as claimed in claim 1 further comprising:
determining a number of machining operations based on an amount of deformation deduced from the difference in propagation velocity calculated in step d.

* * * * *